United States Patent [19]  [11] 4,295,983
Papay et al.                   [45] Oct. 20, 1981

[54] LUBRICATING OIL COMPOSITION CONTAINING BORONATED N-HYDROXYMETHYL SUCCINIMIDE FRICTION REDUCERS

[75] Inventors: Andrew G. Papay, Manchester; Joseph P. O'Brien, Kirkwood, both of Mo.

[73] Assignee: Ethyl Corporation, Richmond, Va.

[21] Appl. No.: 158,715

[22] Filed: Jun. 12, 1980

[51] Int. Cl.³ .............................................. C10M 1/10
[52] U.S. Cl. ............................. 252/49.6; 260/326.5 A
[58] Field of Search ......................... 252/49.6, 51.5 A; 260/326.5 A

[56] References Cited

U.S. PATENT DOCUMENTS

| | | | |
|---|---|---|---|
| 2,611,746 | 9/1952 | Kipp | 252/49.6 |
| 3,037,051 | 5/1962 | Stromberg | 252/51.5 A X |
| 3,087,936 | 4/1963 | Le Suer | 252/49.6 X |
| 3,219,666 | 11/1965 | Norman et al. | 252/51.5 A X |
| 3,254,025 | 5/1966 | Le Suer | 252/49.6 X |
| 3,505,226 | 4/1970 | Cyba | 252/49.6 |
| 3,879,306 | 4/1975 | Kablaoui et al. | 252/51.5 A |
| 4,097,389 | 6/1978 | Andress, Jr. | 252/51.5 A |
| 4,104,182 | 8/1978 | Chou et al. | 252/51.5 A |

Primary Examiner—Andrew Metz
Attorney, Agent, or Firm—Donald L. Johnson; John F. Sieberth; Joseph D. Odenweller

[57] ABSTRACT

Engine fuel economy is improved by adding a friction-reducing amount of a boronated N-hydroxymethyl aliphatic hydrocarbyl succinimide to the engine crankcase oil.

16 Claims, No Drawings

LUBRICATING OIL COMPOSITION CONTAINING BORONATED N-HYDROXYMETHYL SUCCINIMIDE FRICTION REDUCERS

BACKGROUND OF THE INVENTION

In order to conserve energy, automobiles are now being engineered to give improved gasoline mileage compared to those in recent years. This effort is of great urgency as a result of Federal regulations recently enacted which compel auto manufacturers to achieve prescribed gasoline mileage. These regulations are to conserve crude oil. In an effort to achieve the required mileage, new cars are being down-sized and made much lighter. However, there are limits in this approach beyond which the cars will not accommodate a typical family.

Another way to improve fuel mileage is to reduce engine friction. The present invention is concerned with this latter approach.

Lubricating oil containing high molecular weight alkenyl succinimides of ethanolamine in which the alkenyl group contains at least 50 carbon atoms is disclosed in U.S. Pat. No. 3,219,666. They function as dispersants. Lubricating oil containing lower molecular weight alkenyl succinic esteramides of $C_{3-12}$ hydroxyalkylamine is reported in U.S. Pat. No. 3,037,051. They function as corrosion inhibitors. Automatic transmission fluid containing N-hydroxyalkyl succinamic acid is disclosed in U.S. Pat. No. 3,879,306. Boronated alkenyl succinimides of ethanolamines and higher alkanolamines in which the alkenyl group contains at least 50 carbon atoms are disclosed in U.S. Pat. No. 3,087,936.

SUMMARY

According to the present invention, fuel efficient motor oil is provided which contains a friction-reducing amount of a boronated N-hydroxymethyl $C_{12-36}$ aliphatic hydrocarbyl succinimide.

DESCRIPTION OF THE PREFERRED EMBODIMENTS

A preferred embodiment of the invention is a lubricating oil composition formulated for use in the crankcase of an internal combustion engine said composition comprising a major amount of a lubricating oil and a minor friction-reducing amount of an oil-soluble additive comprising the reaction product of an N-hydroxymethyl aliphatic hydrocarbyl succinimide wherein said hydrocarbyl group contains about 12–36 carbon atoms with a boronating agent.

The succinimides have the formula:

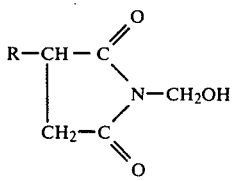

wherein R is an aliphatic hydrocarbon group containing about 12–36 carbon atoms, more preferably 16–22 carbon atoms. The group R can be any alkyl or alkenyl group. Examples of these are: n-dodecyl, n-dodecenyl, 2-ethyl dodecyl, n-tetradecenyl, n-hexadecyl, 2-butyl tetradecyl, n-octadecenyl, 2-ethyl octadecyl, 1-hexyl tetradecenyl, n-eicosenyl, n-docosyl, n-triacontenyl, 1-butyl triacontenyl, 2-hexyl triacontenyl, n-hexatriacontenyl.

The R group can also be derived from polymers of lower olefins such as propylene and isobutylene. Examples of these are propylene tetramer, propylene pentamer, triisobutylene and the like.

In a highly preferred embodiment the aliphatic hydrocarbon group is bonded to the succinic group at a secondary carbon atom. These compounds have the formula:

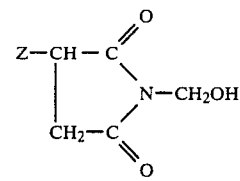

wherein Z is the group:

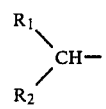

wherein $R_1$ and $R_2$ are independently selected from the group consisting of branched and straight chain hydrocarbon groups containing 1 to about 34 carbon atoms such that the total number of carbon numbers in $R_1$ and $R_2$ is about 11–35. Examples of these additives are:

N-hydroxymethyl 1-ethyltetradecyl succinimide
N-hydroxymethyl 1-methylpentadecenyl succinimide
N-hydroxymethyl 1,2-dimethyl octadecenyl succinimide
N-hydroxymethyl 1-methyl-3-ethyl dodecenyl succinimide
N-hydroxymethyl 1-decyl-2-methyl dotriacontyl succinimide In a more highly preferred embodiment $R_1$ and $R_2$ are straight chain aliphatic hydrocarbon groups. Additives made from these have improved solubility in lubricating oil. Examples of these succinimides are:

N-hydroxymethyl 1-methylpentadecyl succinimide
N-hydroxymethyl 1-propyltridecenyl succinimide
N-hydroxymethyl 1-pentyltridecenyl succinimide
N-hydroxymethyl 1-tetradecyleicosenyl succinimide
N-hydroxymethyl 1-tridecylpentadecenyl succinimide The above highly preferred succinimide intermediates are preferably made from linear α-olefins containing about 12–36 carbon atoms by isomerizing the α-olefins to form a mixture of internal olefins, reacting this mixture of internal olefins with maleic acid, anhydride or ester forming an intermediate, reacting the intermediate with ammonia to form imide, and reacting this with formaldehyde to form the N-hydroxymethyl derivative.

Additives made from isomerized linear α-olefins have improved oil solubility compared with additives made with linear α-olefins.

Isomerization of the linear α-olefin can be carried out using conventional methods. One suitable method is to heat the linear α-olefin with an acidic catalyst. Especially useful acid catalysts are the sulfonated styrene-divinylbenzene copolymers. Such catalysts are commercially available and are conventionally used as cation exchange resins. In the present method they are used in their acid form. Typical resins are Amberlyst 15, XN-1005 and XN-1010 (registered trademarks) available from Rohm and Haas Company. Use of such resins for isomerizing linear α-olefins is described in U.S. Pat. No. 4,108,889, incorporated herein by reference.

N-hydroxymethyl hydrocarbylsuccinimides are readily made by reacting an appropriate $C_{12-36}$ aliphatic hydrocarbyl succinimide with formaldehyde. The following examples illustrate the preparation of the aliphatic hydrocarbylsuccinimides and the conversion of these to their N-hydroxymethyl derivative.

EXAMPLE 1

In a reaction vessel was placed 185 grams of octadecenyl succinic anhydride. This was melted by heating to 60° C. and $NH_3$ was injected. An exothermic reaction proceeded raising the temperature to 160° C. with additional heating. After the reaction ceased the product was heated to 180° C. under 29″ Hg vacuum to remove volatiles. The product was octadecenyl succinimide.

EXAMPLE 2

In a reaction vessel was placed 1 liter of heptane and 550 grams of octadecenyl succinimide. The mixture was heated to 70° C. with stirring and a mixture of 137 grams of 36% aqueous formaldehyde and 22 grams of sodium bicarbonate was added. This mixture was stirred at reflux for 4 hours. Then 300 ml of water was added and the mixture neutralized with hydrochloric acid. The aqueous layer was separated and removed, then 500 ml butanol was added to the organic layer and the mixture washed with hot water. The organic layer was separated and heptane, butanol and residual water distilled off leaving as the product N-hydroxymethyl-n-octadecenyl succinimide.

EXAMPLE 3

In a reaction vessel was placed 1000 grams of linear α-octadecene. To this was added 187 grams Amberlyst 15 (5% moisture). The mixture was stirred under nitrogen and heated at 120° C. for 3 hours. The isomerized product contained 3.6 wt % olefin dimer and the balance was internal $C_{18}$ olefin. The product was separated from the resin.

In a second reaction vessel was placed 504 grams of the above isomerized $C_{18}$ olefin and 300 ml heptane. The heptane was distilled out under vacuum to remove water. Then 2.4 grams of tri-(3,5-di-tert-butyl-4-hydroxybenzyl)mesitylene stabilizer was added. The mixture was heated under nitrogen to 225° C. Then 160 grams of molten maleic anhydride was slowly added over a 2.5-hour period. The mixture was stirred at 225° C. for two more hours and then unreacted maleic anhydride was distilled out by pulling vacuum to 30″ Hg while holding the reaction mixture at 200° C. The product was principally secondary $C_{18}$ alkenyl succinic anhydride.

In a separate reaction vessel was placed 532.5 grams of the above isomerized octadecenyl succinic anhydride. This was heated under nitrogen to 165° C. and then ammonia was injected causing the temperature to rise to 180° C. Ammonia injection was continued until exotherm stopped. The mixture was heated at 170° C. under vacuum to remove water yielding isomerized octadecenyl succinimide. This can then be reacted with formaldehyde as in Example 2 to form N-hydroxymethyl isomerized octadecenyl succinimide.

EXAMPLE 4

In a reaction vessel was placed 1005 grams of linear α-eicosene and 187 grams of Amberlyst 15 (5% moisture). The mixture was heated under nitrogen at 110°–125° C. for 6 hours. The product was internally unsaturated eicosene containing 3.3% eicosene dimer.

In a separate reaction vessel was placed 560 grams of the above isomerized eicosene and 200 ml heptane. The 3.1 grams of tri-(3,5-di-tert-butyl-4-hydroxybenzyl)-mesitylene stabilizer was added and the mixture heated to 210° C. Over a 2.5-hour period, 156.8 grams of maleic anhydride was added at about 225° C. Following this unreacted maleic anhydride was distilled out under vacuum at 210° C. leaving isomerized eicosenyl succinic anhydride.

In another reaction vessel was placed 570 grams of the above isomerized eicosenyl succinic anhydride. This was heated to 160° C. and ammonia injection started. The temperature rose to 175° C. Ammonia injection was continued at 175° C. until the temperature dropped. Then 30″ Hg vacuum was slowly applied to distill out water and ammonia. Additional ammonia was injected to be sure no anhydride remained. There was no further reaction so this ammonia was stripped out at 30″ Hg vacuum at 170° C. yielding isomerized eicosenyl succinimide. This can then be reacted with formaldehyde as in Example 2 to form N-hydroxymethyl isomerized eicosenyl succinimide.

EXAMPLE 5

In a reaction vessel was placed 1100 grams of linear $C_{16}$–$C_{18}$ α-olefin mixture. The olefin mixture was isomerized following the procedure in Example 4.

In a separate vessel was placed 485 grams (2 moles) of the above isomerized olefin. This was heated at 100° C. under 30″ Hg vacuum to remove water. To it was then added 2.4 grams tri-(3,5-di-tert-butyl-4-hydroxybenzyl)-mesitylene. The mixture was heated under nitrogen to 225° C. and then 152 grams of molten maleic anhydride was added over a 3-hour period. The mixture was stirred 30 minutes at 225° C. and an additional 50 grams of maleic anhydride was added. This mixture was stirred 30 minutes at 225° C. following which unreacted maleic anhydride was distilled out at 200° C. under 30″ Hg vacuum.

In a separate reaction vessel was placed 598 grams of the above isomerized $C_{16}$–$C_{18}$ alkenyl succinic anhydride. Ammonia injection was started at 140° C. raising the temperature to 145° C. Ammonia injection was continued at 130° C. until no further ammonia was adsorbed. The mixture was then heated to 180° C. to distill out water and ammonia yielding isomerized $C_{16}$–$C_{18}$ alkenyl succinimide. This can then be reacted with formaldehyde as in Example 2 to form N-hydroxymethyl isomerized $C_{16}$–$C_{18}$ α-olefin succinimide.

Boronating agents include all those boron compounds which when reacted with a N-hydroxymethyl hydrocarbyl succinimide form an oil-soluble boron containing additive. The amount of boron imparted to the additive is generally within the range of about 0.1–1.5 weight percent. Unreacted boron agents may be removed by filtration and/or distillation.

The boron compounds useful in reaction with the acylated nitrogen intermediate include boron oxide, boron oxide hydrate, boron trifluoride, boron tribromide, boron trichloride, boron acids such as boronic acid (e.g. alkyl-$B(OH)_2$ or aryl-$B(OH)_2$), boric acid, (i.e.

$H_3BO_3$), tetraboric acid (i.e. $H_2B_4O_7$), metaboric acid (i.e. $HBO_2$), amides of such boron acids, and esters of such boron acids. The use of complexes of a boron trihalide with ethers, organic acids, inorganic acids, or hydrocarbons is a convenient means of introducing the boron reactant into the reaction mixture. Such complexes are known and are exemplified by boron trifluoridediethyl ether, boron trifluoride-phenol, boron trifluoridephosphoric acid, boron trichloride-chloroacetic acid, boron tribromide-dioxane, and boron trifluoride-methyl ether ether.

Specific examples of boronic acids include methyl boronic acid, phenyl-boronic acid, cyclohexyl boronic acid, p-heptylphenyl boronic acid and dodecyl boronic acid.

The boron acid esters include especially mono-, di-, and tri-organic esters of boric acid with alcohols or phenols such as, e.g., methanol, ethanol, isopropanol, cyclohexanol, cyclopentanol 1-octanol, 2-octanol, dodecanol, behenyl alcohol, oleyl alcohol, stearyl alcohol, benzyl alcohol, 2-butyl cyclohexanol, ethylene glycol, propylene glycol, trimethylene glycol, 1,3-butanediol, 2,4-hexanediol, 1,2-cyclohexanediol, 1,3-octanediol, glycerol, pentaerythritol, diethylene glycol, carbitol, cellosolve, triethylene glycol, tripropylene glycol, phenol, naphthol, p-butylphenol, o,p-diheptylphenol, n-cyclohexylphenol, 2,2-bis-(p-hydroxyphenyl)propane, polyisobutene (molecular weight of 1500)-substituted phenol, ethylenechlorohydrin, o-chlorophenol, m-nitrophenol, 6-bromo-octanol, and 7-keto-decanol. Lower alcohols, 1,2-glycols, and 1,3-glycols, i.e., those having less than about 8 carbon atoms are especially useful for preparing the boric acid esters for the purpose of this invention.

Methods for preparing the esters of boron acid are known and disclosed in the art (such as "Chemical Reviews," pages 959–1064, volume 56). Thus, one method involves the reaction of boron trichloride with 3 moles of an alcohol or a phenol to result in a tri-organic borate. Another method involves the reaction of boric oxide with an alcohol or a phenol. Another method involves the direct esterification of tetra boric acid with 3 moles of an alcohol or a phenol. Still another method involves the direct esterification of boric acid with a glycol to form, e.g., a cyclic alkylene borate.

The ammonium salts of boron acids include principally the salts of boric acid with ammonia or lower alkyl amines, i.e., mono-, di-, or tri-alkyl amines having less than 12 carbon atoms in each alkyl radical. Salts of ammonia or such amines with any other boron acid illustrated above are also useful. It is often desirable to use a mixture of an ammonium salt and at least a molar amount of water. Specific examples of the ammonium salts are ammonium salt of boric acid; a mixture of one mole of ammonium salt of boric acid and three moles of water; a mixture of one mole of monomethylamine salt of boric acid and one mole of water; trimethylamine salt of boric acid; di-cyclo-hexylamine salt of boric acid, etc.

The amount of boronating agent reacted should be an amount which is sufficient to impart the desired boron content to the final additive. An excess of boronating agent can be used and that which remains unreacted can be removed from the reaction mixture.

The boronation is conducted by heating the N-hydroxymethyl hydrocarbyl succinimide with the boronating agent. Temperatures should be high enough to cause the desired amount of boron compound to react, but not so high as to cause undesired decomposition of the reactants or products. A useful temperature range is about 50°–200° C.

During boronation borate ester linkages form. When the boronating agent is boric oxide or a boron acid, water forms and is preferably distilled out to cause the reaction to go to completion. When a lower alkyl borate ester is used as the boronating agent, a lower alkanol is formed and is preferably distilled out. When a borate salt such as ammonium borate is used as the boronating agent, both ammonia and water form and are distilled out.

The following examples illustrate the method of boronating the N-hydroxymethyl aliphatic hydrocarbyl succinimide intermediate.

EXAMPLE 6

In a reaction vessel was placed 240.9 grams of N-hydroxymethyl octadecenylsuccinimide. This was heated to about 80° C. to cause it to melt and was mixed with 59.7 grams of trimethyl borate. The stirred mixture was heated to 125° C. over a 4-hour period while distilling out a trimethyl boratemethanol azeotrope at 54°–55° C. Then a 28" vacuum was applied to remove the remaining trimethyl borate. Infrared spectra showed the disappearance of most of the hydroxyl groups and the appearance of borate ester absorption.

EXAMPLE 7

In a reaction vessel was placed 306.5 grams of N-hydroxymethyl octadecenylsuccinimide and 25.2 grams of boric acid ($H_3BO_3$). The mixture was heated to 110° C. and stirred until most of the boric acid dissolved. It was then heated to 125° C. until distilling out water formed by esterification. A vacuum of 29" was applied to remove residual water (total 13 grams water removed). The final product was filtered hot to remove a few granules of solid.

EXAMPLE 8

In a reaction vessel was placed 60 grams of triethyl borate and 190.2 grams of N-hydroxymethyl octadecenylsuccinimide. A 6" Vigraux column was fitted onto the reaction vessel and the mixture was heated under 15" vacuum to distill out ethanol at 60°–62° C. overhead. Pot temperature was gradually raised to 140° C. while distilling out ethanol. Then vacuum was increased to 29" to distill out the remaining triethyl borate. Infrared at $1300-1400^{-1}$ cm showed the formation of borate ester groups.

The products formed are borate esters of N-hydroxymethyl aliphatic hydrocarbyl succinimide. Such esters are characterized in that they contain at least one borate ester group having the structure:

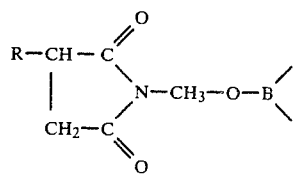

The remaining groups bonded to boron may be the same ester groups shown or may be lower alkoxide, phenoxide, oxide or hydroxyl.

The additives are added to lubricating oil in an amount which reduces the friction of an engine operating with the oil in the crankcase. A useful concentration is about 0.05–3 weight percent. A more preferred range is about 0.1–1.5 weight percent.

From the above it can be seen that the present invention provides an improved crankcase lubricating oil. Accordingly, an embodiment of the invention is an improved motor oil composition formulated for use as a crankcase lubricant in an internal combustion engine wherein the improvement comprises including in the crankcase oil an amount sufficient to reduce fuel consumption of the engine of the present additives.

In a highly preferred embodiment such improved motor oil also contains an ashless dispersant, a zinc dialkyldithiophosphonate and an alkaline earth metal salt of a petroleum sulfonic acid or an alkaryl sulfonic acid (e.g. alkylbenzene sulfonic acid).

The additives can be used in mineral oil or in synthetic oils of viscosity suitable for use in the crankcase of an internal combustion engine. Crankcase lubricating oils have a viscosity up to about 80 SUS at 210° F. According to the present invention the additives function to increase fuel economy when added to lubricating oil compositions formulated for use in the crankcase of internal combustion engines. Similar mileage benefits could be obtained in both spark ignited and diesel engines.

Crankcase lubricating oils of the present invention have a viscosity up to about SAE 40. Sometimes such motor oils are given a classification at both 0° and 210° F., such as SAE 10W 40 or SAE 5W 30.

Crankcase lubricants of the present invention can be further identified since they usually contain a zinc dihydrocarbyldithiophosphate in addition to the present additive. Likewise, these crankcase lubricants contain an alkaline earth metal sulfonate such as calcium petroleum sulfonate, calcium alkaryl sulfonate, magnesium petroleum sulfonate, magnesium alkaryl sulfonate, barium petroleum sulfonate, barium alkaryl sulfonate and the like.

Mineral oils include those of suitable viscosity refined from crude oil from all sources including Gulfcoast, midcontinent, Pennsylvania, California, Alaska and the like. Various standard refinery operations can be used in processing the mineral oil.

Synthetic oil includes both hydrocarbon synthetic oil and synthetic esters. Useful synthetic hydrocarbon oils include liquid polymers of $\alpha$-olefins having the proper viscosity. Especially useful are the hydrogenated liquid oligomers of $C_{6-12}$ $\alpha$-olefins such as $\alpha$-decene trimer. Likewise, alkylbenzenes of proper viscosity can be used, such as didodecylbenzene.

Useful synthetic esters include the esters of both monocarboxylic acid and polycarboxylic acid as well as monohydroxy alkanols and polyols. Typical examples are didodecyl adipate, trimethylolpropane tripelargonate, pentaerythritol tetracaproate, di-(2-ethylhexyl)adipate, dilauryl sebacate and the like. Complex esters prepared from mixtures of mono- and dicarboxylic acid and mono- and polyhydroxyl alkanols can also be used.

Blends of mineral oil with synthetic oils are particularly useful. For example, blends of 10–25 weight percent hydrogenated $\alpha$-decene trimer with 75–90 weight percent 150 SUS (100° C.) mineral oil results in an excellent lubricant. Likewise, blends of about 10–25 weight percent di-(2-ethylhexyl)adipate with mineral oil of proper viscosity results in a superior lubricating oil. Also blends of synthetic hydrocarbon oil with synthetic esters can be used. Blends of mineral oil with synthetic oil are especially useful when preparing low viscosity oil (e.g. SAE 5W 20) since they permit these low viscosities without contributing excessive volatility.

The more preferred lubricating oil composition includes zinc dihydrocarbyldithiophosphate (ZDDP) in combination with the present additives. Both zinc dialkyldithiophosphates and zinc dialkaryldithiophosphates as well as mixed alkyl-aryl ZDDP are useful. A typical alkyl-type ZDDP contains a mixture of isobutyl and isoamyl groups. Zinc dinonylphenyldithiophosphate is a typical aryl-type ZDDP. Good results are achieved using sufficient ZDDP to provide about 0.01–0.5 weight percent zinc. A preferred concentration supplies about 0.05–0.3 weight percent zinc.

Another additive used in the oil compositions are the alkaline earth metal petroleum sulfonates or alkaline earth metal alkaryl sulfonates. Examples of these are calcium petroleum sulfonates, magnesium petroleum sulfonates, barium alkaryl sulfonates, calcium alkaryl sulfonates or magnesium alkaryl sulfonates. Both the neutral and the overbased sulfonates having base numbers up to about 400 can be beneficially used. These are used in an amount to provide about 0.05–1.5 weight percent alkaline earth metal and more preferably about 0.1–1.0 weight percent. In a most preferred embodiment the lubricating oil composition contains a calcium petroleum sulfonate or alkaryl (e.g. alkylbenzene) sulfonate.

Viscosity index improvers can be included such as the polyalkylmethacrylate type or the ethylene-propylene copolymer type. Likewise, styrene-diene VI improvers or styrene-acrylate copolymers can be used. Alkaline earth metal salts of phosphosulfurized polyisobutylene are useful.

Most preferred crankcase oils also contain an ashless dispersant such as the polyolefin-substituted succinamides and succinimides of polyethylene polyamines such as tetraethylenepentamine. The polyolefin succinic substituent is preferably a polyisobutene group having a molecular weight of from about 800 to 5,000. Such ashless dispersants are more fully described in U.S. Pat. No. 3,172,892 and U.S. Pat. No. 3,219,666 incorporated herein by reference.

Another useful class of ashless dispersants are the polyolefin succinic esters of mono- and polyhydroxy alcohols containing 1 to about 40 carbon atoms. Such dispersants are described in U.S. Pat. No. 3,381,022 and U.S. Pat. No. 3,522,179.

Likewise, mixed ester/amides of polyolefin substituted succinic acid made using alkanols, amines and/or aminoalkanols represent a useful class of ashless dispersants. Typical examples of these are described in U.S. Pat. No. 3,184,474; U.S. Pat. No. 3,576,743; U.S. Pat. No. 3,632,511; U.S. Pat. No. 3,804,763; U.S. Pat. No. 3,948,800 and U.S. Pat. No. 3,950,341.

The succinic amide, imide and/or ester type ashless dispersants may be boronated by reaction with a boron compound such as boric acid. Likewise, the succinic amide, imide, and/or ester may be oxyalkylated by reaction with an alkylene oxide such as ethylene oxide or propylene oxide.

Other useful ashless dispersants include the Mannich condensation products of polyolefin-substituted phenols, formaldehyde and polyethylene polyamine. Preferably, the polyolefin phenol is a polyisobutylene-substituted phenol in which the polyisobutylene group has a molecular weight of from about 800 to 5,000. The preferred polyethylene polyamine is tetraethylene pentamine. Such Mannich ashless dispersants are more fully described in U.S. Pat. Nos. 3,368,972; 3,413,347; 3,442,808; 3,448,047; 3,539,633; 3,591,598; 3,600,372; 3,634,515; 3,697,574; 3,703,536; 3,704,308; 3,725,480; 3,726,882; 3,736,357; 3,751,365; 3,756,953; 3,792,202; 3,798,165; 3,798,247 and 3,803,039.

The above Mannich dispersants can be reacted with boric acid to form boronated dispersants having improved corrosion properties.

Good results are obtained by using the present additives in crankcase lubricating oil in combination with a phosphonate additive. Preferred phosphonates are the di-$C_{1-4}$ alkyl $C_{12-36}$ alkyl or alkenyl phosphonates. These compounds have the structure:

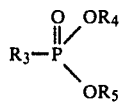

wherein $R_3$ is an aliphatic hydrocarbon group containing about 12–36 carbon atoms and $R_4$ and $R_5$ are independently selected from lower alkyl groups containing about 1–4 carbon atoms. Representative examples of these coadditives are:
dimethyl octadecylphosphonate
dimethyl octadecenylphosphonate
diethyl 2-ethyldecylphosphonate
ethyl propyl 1-butylhexadecylphosphonate
methyl ethyl octadecylphosphonate
methyl butyl eicosylphosphonate
dimethyl hexatriacontylphosphonate When using the phosphonate coadditive only a small amount is required. A useful range is about 0.005–0.75 weight percent based on the formulated oil. A more preferred amount is about 0.05–0.5 weight percent.

In commercial practice a preferred way to add the present additives to lubricating oil is in the form of an additive package. These are concentrates dissolved in oil which when added to a base oil will provide an effective concentration of the present additive and other known additives. For example, if the desired use level is 0.2 weight percent and the final formulated oil is made by adding 10 parts of additive package to 90 parts of base lubricating oil, then the additive pack will contain 2.0 weight percent of the present additive.

In addition to the present additives, such additive packages usually contain an ashless dispersant such as those previously discussed. In addition, the additive package may contain the phosphonate coadditive, a zinc dialkyldithiophosphate, an alkaline earth metal hydrocarbonsulfonate (either neutral or overbased), an alkaline earth metal phenate (either neutral or overbased), or similar sulfur-bridged phenates, an antioxidant such as 4,4'-methylenebis-(2,6-di-tert-butylphenol) or N-octylphenyl-α-naphthylamine, a phosphosulfurized terpene or olefin such as phosphosulfurized polyisobutylene (mol wt 1000) or alkaline earth metal salts of such phosphosulfurized olefin, a viscosity index improver such as a polyalkylmethacrylate, an ethylene/propylene copolymer, an ethylene/propylene/non-conjugated diene terpolymer, a styrene/conjugated diene copolymer, a styrene/acrylate copolymer and the like may be included in the package or may be added separately to the oil.

The following formulation illustrates a typical additive package of this invention. Parts are by weight.

| | |
|---|---|
| boronated N-hydroxymethyl-octadecenylsuccinimide polyisocutenyl (mol wt 950) | 1.2–12 parts |
| succinimide of tetraethylene-pentamine | 2.9–120 parts |
| zinc dialkyldithiophosphate (10% Zn) | 2.9–120 parts |
| calcium alkyl benzene sulfonate (TBN 300) | 12.0–60 parts |
| dimethyloctadecylphosphonate | 1.2–12 parts |
| Acryloid 702 [1] | 60.0–180 parts |
| neutral 100 SUS mineral oil | 5.0–50 parts |

[1] registered trademark for Rohm and Haas Company brand of polymethacrylate VI improver Tests were conducted which demonstrated the friction reducing properties of the present invention.

LFW-1 TEST

In this test a metal cylinder is rotated around its axis 45° in one direction and then 45° in the opposite direction at a rate of 120 cycles per minute. A metal block curved to conform to the circular contour of the cylinder presses at a fixed load against the periphery of the cylinder. Test lubricant is applied to the rubbing surface between the cylinder and the block. Torque transmitted to the block from the oscillating cylinder is measured. The greater the torque the greater the friction. Results are given in terms of "percent improvement" which is the percent reduction in torque compared to that obtained with the test oil without the test additive.

The test oil is a fully formulated oil of SAE SE quality. Test results are given in the following table:

| Additive | Improvement |
|---|---|
| Example 7 (0.5%) | 12.3%, 11.6% [1] |
| Example 8 (0.5%) | 13.7%, 12.8% |

[1] Replicate runs

These results show a significant reduction in friction.

We claim:
1. A friction reducing lubricating oil additive comprising the reaction product of an N-hydroxymethyl aliphatic hydrocarbyl succinimide with an amount of a boronating agent sufficient to impart about 0.1 to 1.5 weight percent boron to said reaction product, said reaction product being made at about 50°–200° C., said N-hydroxymethyl aliphatic hydrocarbyl succinimide prepared by reacting $NH_3$ with an aliphatic $C_{12}$–$C_{36}$ hydrocarbyl succinic anhydride to form the corresponding succinimide and subsequently reacting the succinimide with formaldehyde to form said N-hydroxymethyl aliphatic hydrocarbyl succinimide.

2. An additive of claim 1 wherein said boronating agent is selected from the group consisting of boron acid, boron oxide, esters of boron acid, boron acid salts, boron halide and mixtures of the foregoing.

3. An additive of claim 2 wherein said hydrocarbyl group contains about 16–22 carbon atoms.

4. An additive of claim 3 wherein said boronating agent is a lower alkyl borate ester.

5. An additive of claim 3 wherein said boronating agent is boric acid.

6. An additive of claim 1 which is the reaction product of N-hydroxymethyl octadecenylsuccinimide with a boronating agent.

7. An additive of claim 6 wherein said boronating agent is a lower alkyl borate ester.

8. An additive of claim 6 wherein said boronating agent is boric acid.

9. Lubricating oil formulated for use in the crankcase of an internal combustion engine containing a friction-reducing amount of the reaction product of claim 1.

10. A lubricating oil composition of claim 9 wherein said boronating agent is selected from the group consisting of boron acids, boron oxides, esters of boron acids, boron acid salts, boron halides and mixtures of the foregoing.

11. A lubricating composition of claim 10 wherein said hydrocarbyl group contains about 16–22 carbon atoms.

12. A lubricating oil composition of claim 11 wherein said boronating agent is a lower alkyl borate ester.

13. A lubricating oil composition of claim 11 wherein said boronating agent is boric acid.

14. A lubricating oil composition of claim 9 wherein said reaction product is the reaction product of N-hydroxymethyl octadecenylsuccinimide with a boronating agent.

15. A lubricating oil composition of claim 14 wherein said boronating agent is a lower alkyl borate ester.

16. A lubricating oil composition of claim 14 wherein said boronating agent is boric acid.

* * * * *

UNITED STATES PATENT AND TRADEMARK OFFICE
CERTIFICATE OF CORRECTION

PATENT NO. : 4,295,983
DATED : October 20, 1981
INVENTOR(S) : Andrew G. Papay et al It is certified that error appears in the above-identified patent and that said Letters Patent are hereby corrected as shown below:

Cover page: "(73) Assignee: Ethyl Corporation
Richmond, Va."

should be

-- (73) Assignee: Edwin Cooper, Inc.
St. Louis, Mo.

Signed and Sealed this

Thirteenth Day of July 1982

[SEAL]

Attest:

*Attesting Officer*

GERALD J. MOSSINGHOFF
*Commissioner of Patents and Trademarks*